(12) United States Patent
Laghi et al.

(10) Patent No.: US 11,478,419 B2
(45) Date of Patent: Oct. 25, 2022

(54) TOPICAL COMPOSITION CONTAINING ANTIOXIDANTS

(71) Applicants: Aldo Laghi, Pinellas Park, FL (US); Alps South Europe, S.R.O. Božkovské náměstí 17/21, Plzen (CZ)

(72) Inventors: Aldo Laghi, Pinellas Park, FL (US); Nathaniel Vint, Palm Harbor, FL (US)

(73) Assignee: ALPS SOUTH EUROPE, S.R.O., Plzen (CZ)

(*) Notice: Subject to any disclaimer, the term of this patent is extended or adjusted under 35 U.S.C. 154(b) by 87 days.

(21) Appl. No.: 16/691,642

(22) Filed: Nov. 22, 2019

(65) Prior Publication Data

US 2021/0154134 A1 May 27, 2021

(51) Int. Cl.
| | | |
|---|---|---|
| *A61K 9/00* | (2006.01) | |
| *A61K 9/107* | (2006.01) | |
| *A61K 47/14* | (2017.01) | |
| *A61K 47/44* | (2017.01) | |
| *A61K 47/10* | (2017.01) | |
| *A61K 31/355* | (2006.01) | |
| *A61K 8/06* | (2006.01) | |
| *A61K 8/67* | (2006.01) | |
| *A61K 47/18* | (2017.01) | |
| *A61Q 19/08* | (2006.01) | |

(52) U.S. Cl.
CPC ............ *A61K 9/0014* (2013.01); *A61K 8/062* (2013.01); *A61K 8/678* (2013.01); *A61K 9/107* (2013.01); *A61K 31/355* (2013.01); *A61K 47/10* (2013.01); *A61K 47/14* (2013.01); *A61K 47/18* (2013.01); *A61K 47/44* (2013.01); *A61K 2800/522* (2013.01); *A61K 2800/524* (2013.01); *A61Q 19/08* (2013.01)

(58) Field of Classification Search
CPC ...................................................... A61K 47/44
See application file for complete search history.

(56) References Cited

U.S. PATENT DOCUMENTS

| | | | |
|---|---|---|---|
| 10,543,167 B2* | 1/2020 | Laghi | ............ A61K 8/062 |
| 2016/0008262 A1* | 1/2016 | Hein | ............ A61Q 19/00 |
| | | | 424/70.1 |
| 2016/0074319 A1* | 3/2016 | Laghi | ............ A61K 9/0014 |
| | | | 514/533 |

OTHER PUBLICATIONS

Wypyeh, Handbook of UV Degradation of Stabilization, 2nd ed., Chem Tec Publishing 2015, p. 108. (Year: 2015).*

* cited by examiner

*Primary Examiner* — Gina C Justice
(74) *Attorney, Agent, or Firm* — Cole Carlson

(57) ABSTRACT

Compositions for topical application that effectively deliver antioxidants across the epidermis, dermis, or a combination thereof into cells and/or the bloodstream while concurrently maintaining chemical activity of the antioxidants. In certain aspects, these formulations include emulsions and balms each having a lipophilic carrier and a lipophilic antioxidant solubilized by the lipophilic carrier. Also disclosed herein are methods for making these compositions for topical application.

7 Claims, 1 Drawing Sheet

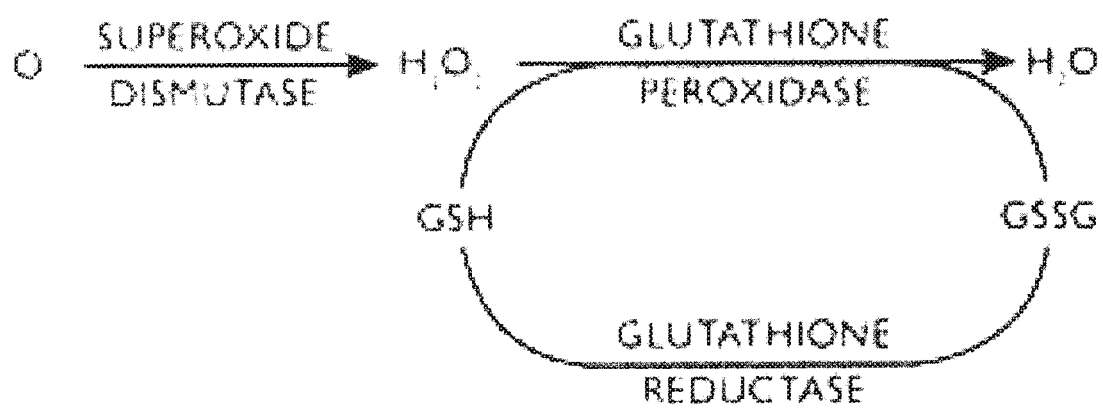

TOPICAL COMPOSITION CONTAINING ANTIOXIDANTS

CROSS-REFERENCE TO RELATED INVENTIONS

This Application is a continuation of U.S. patent application Ser. No. 14/711,383 titled "Topical Composition Containing Antioxidants" filed on May 13, 2015 which claims priority to U.S. Provisional Patent Application No. 62/051,534 filed on Sep. 17, 2014, the contents of which are incorporated by reference herein in their entirety.

BACKGROUND OF THE INVENTION

Field of the Invention

The present invention relates generally to the field of compositions for topical applications, and more particularly, to compositions having lipophilic, phenolic antioxidants.

Description of the Background Art

Reactive Oxygen Species (ROS) are chemically reactive molecules, which include oxygen, superoxides, and various peroxides (e.g., $O_2$, $O_2^-$, $O_2^{2-}$, peroxy radicals, $H_2O_2$, etc.). In mammals, ROS are generated (1) as a natural by-product of oxidative metabolism, (2) in response to environmental stress, or (3) a combination thereof. Although ROS can be a natural by-product of cellular processes, ROS include free radicals that can damage cells by inducing deleterious chemical reactions and cell-signaling pathways. For example, in humans, these ROS-induced chemical reactions and cell-signaling pathways are often associated with aging, apoptosis (programmed cell death), and illnesses (e.g., various skin conditions and autoimmune disorders including psoriasis, amytrophic lateral sclerosis, multiple sclerosis, muscular dystrophy, etc.).

Although ROS are associated with inducing deleterious cellular processes, numerous cellular defense mechanisms in humans exist to minimize damage often associated with ROS. For example, human cells include various enzymes such as alpha-1-microglobulin, superoxide dismutases, catalases, lactoperoxidases, glutathione peroxidases and peroxiredoxins, which essentially convert potentially harmful ROS and free radicals into potentially useful chemical molecules that may be re-used by a cell during various cellular processes. For example, FIG. 1 illustrates one such endogenous biochemical pathway in which ROS (i.e., $O_2^-$) is chemically modified by superoxide dismutase into hydrogen peroxide ($H_2O_2$), and hydrogen peroxide is subsequently converted by glutathione peroxidase into water ($H_2O$). Thus, FIG. 1 clearly depicts an exemplary, endogenous biochemical pathway in which a cell naturally defends against ROS and free radicals by converting potentially harmful $O_2$ and $H_2O_2$ into $H_2O$.

Although FIG. 1 illustrates natural defense mechanisms against ROS, these endogenous natural defense mechanisms can become overwhelmed during times of increased cellular stress (e.g., times of increased oxidative metabolism or times of increased environmental stress), which can lead to the increased presence of ROS. Likewise, when a person is deficient in certain enzymes that counteract ROS, ROS can be found in increased cellular levels within these particular individuals.

Due to the deleterious processes (e.g., aging, apoptosis, etc.) and illnesses associated with increased levels of ROS, supplementation with substances that counteract ROS and the deleterious processes and diseases associated therewith has long been sought. For example, many believe that supplementation with vitamins and various antioxidants may beneficially counteract the deleterious processes associated with ROS. In theory and further based on in vitro experimentation, it is known that antioxidants can act as hydrogen donors to ROS (e.g., peroxy radicals) to essentially neutralize free radicals. Based on this theory, it is further thought that antioxidants are viable substances to potentially minimize the effects of ROS in vivo.

While supplementation with antioxidants seems like a viable option to minimize the deleterious effects associated with ROS, numerous problems currently exist with such supplementation. For example, many antioxidant formulations are designed for oral administration (e.g., in pill, tablet, or capsule form). However, these oral formulations are ineffective because the vast majority of these orally administered antioxidants are rendered inactive by chemical degradation occurring either in the stomach or duodenum before being absorbed into the blood stream. Thus, for at least this reason, oral administration of antioxidants (via pills, tablets, or capsules) is ineffective.

In addition to oral antioxidant formulations mentioned above, certain transdermal and transmucosal antioxidant formulations also exist. However, similar to the oral formulations mentioned above, these transdermal and transmucosal formulations also have numerous problems. For example, many of these transdermal and transmucosal formulations include hydrophilic, lipophobic antioxidants. Because of the inherent chemical properties of the hydrophilic, lipophobic antioxidants included within these transdermal and transmucosal formulations, these antioxidants are solvated in water-based solutions (or an aqueous, water phase of specific formulation). Because these hydrophilic, lipophobic antioxidants are solvated in water-based solutions, crossing lipophilic biological membranes, such as mucous membranes or the epidermis/dermis, poses a major problem. Specifically, efficient delivery of these antioxidants poses a major problem due to the high lipid content of these membranes. For at least this reason, current transdermal and transmucosal formulations that administer the above-described antioxidants are ineffective.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

Therefore, a need exists to provide a composition that effectively delivers antioxidants while avoiding the degradative processes discussed above. More particularly, a need exists to provide a transdermal formulation that effectively delivers antioxidants across the epidermis, dermis, or a combination thereof into cells and/or the bloodstream while concurrently maintaining chemical activity of these antioxidants. Provided herein are compositions for topical application that effectively deliver antioxidants across the epidermis, dermis, or a combination thereof into cells and/or the bloodstream while concurrently maintaining the antioxidant's chemical activity.

In certain aspects, these formulations include emulsions for topical application. These emulsions may include a water phase ranging 60-90%, 65-85%, or 70-80% of the overall emulsion, and an oil phase. The oil phase may include, for example, a lipophilic carrier and a lipophilic antioxidant solubilized by the lipophilic carrier, and the lipophilic carrier and the lipophilic antioxidant being present from 1:1 to 20:1, 1:1 to 15:1, 1:1 to 10:1, 1:1 to 5:1, 1:1 to 3:1, or 1:1 to 2:1 of lipophilic carrier to lipophilic antioxidant in the emulsion. The lipophilic antioxidant includes one of the following formulas (I) to (III):

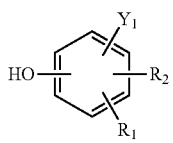

FORMULA I

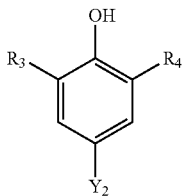

FORMULA II

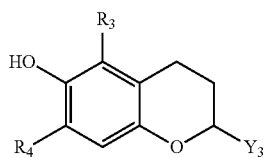

FORMULA III

In this aspect, $R_1$ represents a $C_1$ to $C_9$ linear or branched alkyl group, styrene, or H. $R_2$ is optional and represents a $C_1$ to $C_6$ linear or branched alkyl group, styrene, or H. $Y_1$ represents a $C_1$ to $C_6$ linear or branched alkyl group, H, styrene, —$SR_5$, or —$(CH_2)_n COOR_6$. $R_3$ and $R_4$ independently represent a $C_1$ to $C_6$ branched alkyl or H. $Y_2$ represents a $C_1$ to $C_6$ linear or branched alkyl group, $SR_5$, or —$(CH_2)_n COOR_6$, or H. $Y_3$ represents a linear or branched alkyl group. "n" is from 1 to 10. $R_5$ represents H, isoprene, a methyl group, an ethyl group, a propyl, a butyl, a pentyl group, a hexyl group, an isopropyl group, an isobutyl group, a sec-butyl group, a tert-butyl group, a tert-pentyl group, a neo-pentyl group, an isopentyl group, an isohexyl group, a neohexyl group, styrene, or

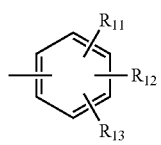

$R_{11}$, $R_{12}$, and $R_{13}$ independently represent OH, a methyl group, ethyl group, a propyl group, a butyl group, an isopropyl group, a tert-butyl group, an isoprene, tert-pentyl group, or H. $R_6$ represents an alkyl group having $C_{10}$ to $C_{30}$, and wherein formulas (I) to (III) include pharmaceutically acceptable salts thereof.

In this aspect, the $C_1$ to $C_6$ linear or branched alkyl groups of $Y_1$ and $Y_2$ are substituted with

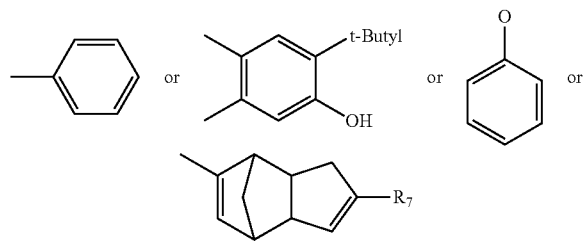

and wherein $R_7$ represents

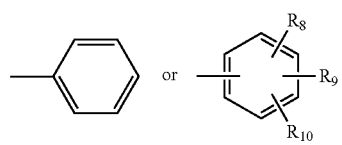

and wherein $R_8$, $R_9$, and $R_{10}$ independently represent OH, a methyl group, ethyl group, a propyl group, a butyl group, an isopropyl group, a tert-butyl group, an isoprene, a tert-pentyl group, or H; and at least one of $R_8$, $R_9$, and $R_{10}$ is OH; and $R_8$, $R_9$, and $R_{10}$ can be in any of the ortho, meta, and para positions relative to each other.

In certain aspects, the emulsion includes at least two lipophilic antioxidants from formulas (I) to (III).

In certain aspects, the emulsion includes at least three lipophilic antioxidants from formulas (I) to (III).

In certain aspects, the lipophilic carrier and the lipophilic antioxidant are present from 1:1 to 20:1, 1:1 to 15:1, 1:1 to 10:1, 1:1 to 5:1, 1:1 to 3:1, or 1:1 to 2:1 of lipophilic carrier to lipophilic antioxidant in the emulsion.

In certain aspects, the oil phase ranges from 10-40 wt % of the overall emulsion.

In certain aspects, the oil phase ranges from 15-30 wt % or 20-25 wt % of the overall emulsion.

In certain aspects, the lipophilic carrier includes at least one of a mineral oil, vegetable oil, or combinations thereof.

In certain aspects, the mineral oil is a paraffinic oil, a napthenic oil, or a combination thereof.

In certain aspects, the lipophilic carrier includes at least one selected from the group consisting of argan oil, avocado oil, babassu oil, canola oil, coconut oil, hemp seed oil, jojoba oil, olive oil, and rosehip oil.

In certain aspects, the lipophilic carrier is avocado butter, mango butter, shea butter, cocoa butter, or any combination thereof.

Further disclosed is a balm that is substantially similar to the disclosed emulsions. However, unlike the disclosed emulsions, the balm preferably limits the amounts and/or excludes water within its overall compositions. The balm preferably limits water within its overall composition to include as little as 5 wt % water, 3 wt % water, 1 wt % water, 0.5 wt % water, or no water.

Additionally disclosed are methods of making the emulsions and balms.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 illustrates an exemplary, endogenous biochemical pathway chemically modifying ROS.

DETAILED DESCRIPTION OF THE PREFERRED EMBODIMENT

The present invention will now be described more fully hereinafter. It is to be understood that the aspects described below are not limited to specific compounds, synthetic methods, or uses as such may, of course, vary. It is also to be understood that the terminology used herein is for the purpose of describing particular aspects only and is not intended to be limiting. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

It is understood that any given particular aspect of the disclosed compositions and methods can be easily compared to the specific examples and embodiments disclosed herein. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

Emulsions and Balms

Disclosed are emulsions and balms for topical applications that effectively deliver antioxidants. More particularly, these emulsions and balms are transdermal formulations that deliver lipophilic antioxidants across the epidermis, dermis, or a combination thereof into a subject's cells and/or the bloodstream while concurrently maintaining chemical activity of these antioxidants. "Emulsions" as defined refer to compositions having a mixture of two phases (e.g., an oil-in-water phase or a water-in-oil phase). As disclosed further below, the emulsions may include additional solvents and surfactants to maintain a homogenous dispersion of the two phases within the emulsion. In the disclosed emulsions, the water phase of the emulsion includes a majority of water, which includes greater than 50% water, greater than 60% water, greater than 70% water, greater than 80% water or greater than 90% water, and in certain aspects, the overall water content within the disclosed emulsions may include 30-75 wt %, 35-60 wt %, or 45-55 wt % of the overall weight of the emulsion. In certain aspects, surfactants (e.g., non-ionic surfactants, anionic surfactants, cationic surfactants, or any mixture thereof) are present in an operable concentration of 2-20 wt %, 2-10 wt %, 3-10 wt %, 3-8 wt % of the overall emulsion with the preferable concentration being approximately 3-6%. "Balm" as defined herein refers to a composition that omits the addition of water except for the presence of any residual impurities within the composition. For example, the balms herein may include as little as 5 wt % water, 3 wt % water, 1 wt % water, 0.5 wt % water, or no water in the overall concentration of the balm.

In certain aspects, the disclosed emulsions and balms each include lipophilic carriers and lipophilic antioxidants. The lipophilic carriers disclosed herein are selected to maximize solubility of the lipophilic antioxidants while concurrently minimizing any chemical degradation of the lipophilic antioxidants. For example, in certain aspects, the lipophilic antioxidants are completely solubilized or are solubilized to no less than 98%, 98.5%, 99%, or 99.5% with the disclosed emulsions and balms such that the lipophilic antioxidant does not visibly precipitate out of the balms and emulsions. With regard to the disclosed balms and emulsions, the lipophilic carriers are selected to maximize potency and efficacy of the lipophilic antioxidant. Additionally, the lipophilic carriers are selected to maximize skin penetration efficacy. In other words, the lipophilic carriers allow for efficient penetration of a subject's epidermis and dermis while concurrently minimizing any chemical degradation of the lipophilic antioxidants. Also, it is preferred that the lipophilic carriers are pharmaceutically acceptable carriers.

Within the disclosed balms and emulsions, the lipophilic carrier and lipophilic antioxidant(s) are present at a ratio ranging from 1:1 to 25:1, 1:1 to 20:1, 1:1 to 15:1, 1:1 to 10:1, 1:1 to 5:1, 1:1 to 3:1, or 1:1 to 2:1. More preferably, within the disclosed balms and emulsions, the lipophilic carrier and lipophilic antioxidant(s) are present at a ratio ranging from 1:1 to 10:1. Most preferably, within the disclosed balms and emulsions, the lipophilic carrier and lipophilic antioxidant(s) are present at a ratio ranging from 1:1 to 5:1. These above discussed ratios are preferred because the solution is stable and effective, and when the lipophilic carrier and lipophilic antioxidant(s) are used in ratios outside of those disclosed above, precipitation of solids and/or loss of efficacy disadvantageously occurs.

In certain aspects, the lipophilic carrier ranges from 50-99 wt %, 60-98 wt %, 75-98 wt %, 85-98 wt %, 95-99 wt %, 96-99 wt %, or 96-98 wt % for balm, and 1-50 wt %, 2-40 wt %, 5-35 wt %, 7.5-25 wt % for emulsions of the overall composition. More preferably, the lipophilic carrier ranges from 17-99 wt % for balm, and 5-30 wt % for emulsions of the overall composition. Most preferably, the lipophilic carrier ranges from 90-98 wt % for balm and 10-20 wt % for emulsions of the overall composition. The lipophilic weight percentages above are preferred because concentrations of antioxidant above these percentage do not yield increased efficacy, and when the lipophilic carrier (in combination with the lipophilic antioxidant(s)) is provided in a weight percentage falling outside of those above disclosed ranges, precipitation and or loss of efficacy disadvantageously occurs.

In certain aspects, the lipophilic carriers advantageously include waxes and/or oils that solvate the lipophilic antioxidants while maintaining the chemical activity of lipophilic antioxidants. It is desired for the final product to have a solid or semisolid consistency. Therefore thicker oils and hydrogenated oils, or butters, are preferred. In certain aspects, antioxidant potency and/or efficacy is diminished when the antioxidant is mixed with high molecular weight carriers having a molecular weight (Mw) ranging from 150 to 600, from 200 to 550, from 250 to 500, from 250 to 475, from 250 to 400, from 250 to 350, from 300 to 475, from 350 to 450, and from 400 to 450. In certain aspects, the lipophilic carrier is as beeswax having a molecular weight ranging from 300 to 475, from 350 to 450, or from 400 to 430. In certain aspects, the lipophilic carrier may include avocado butter having a molecular weight ranging from 200 to 350, from 215 to 300, from 240 to 290, or from 260 to 290. In certain aspects, these lipid carriers included within the disclosed formulations can include mineral oils, saturated vegetable oil, unsaturated vegetable oil, or a combination thereof. In certain aspects, it is preferable that the emulsion and balms include one or more of the disclosed lipophilic carriers. In certain aspects, it is preferable that the emulsions and balms include at least two of the disclosed lipophilic carriers. In yet another aspect, it is preferable that the emulsions and balms include three or more of the disclosed lipophilic carriers.

Examples of vegetable oils may include, but are not limited to, argan oil, avocado oil, babassu oil, canola oil, coconut oil, hemp seed oil, jojoba oil, olive oil, and rosehip oil. In certain aspects, the lipophilic carrier includes at least one vegetable oil selected from argan oil, avocado oil, babassu oil, canola oil, coconut oil, hemp seed oil, jojoba oil, olive oil, and rosehip oil. In certain aspects, the lipophilic carrier includes at least two vegetable oils selected from argan oil, avocado oil, babassu oil, canola oil, coconut oil, hemp seed oil, jojoba oil, olive oil, and rosehip oil. In certain aspects the saturated vegetable oils can include butters, which have a higher viscosity than unsaturated oils and are typically solid or semi-solids at room temperature. Examples of saturated oils include, but are not limited to, avocado butter, mango butter, shea butter, cocoa butter, and any combination thereof. In certain aspects, it is advantageous to use the unsaturated vegetable oils in the disclosed emulsions because of their lower viscosities (in comparison to the disclosed butters and waxes). However, it is advantageous to use the saturated oils in the balms due their higher viscosities (in comparison to the disclosed butters and waxes).

Examples of mineral oils may include, but are not limited to, alkane based oils having, preferably, ranging from $C_{15}$ to $C_{40}$ in length (e.g., $C_nH_{2n+1}$). In certain aspects, the mineral oils are petroleum based distillates that include, for example, paraffinic oils, napthenic oils, and combinations thereof. Specific examples of paraffinic oils can include mineral oil, petroleum jelly and paraffin wax. In certain aspects, the balms and emulsions can include two or more paraffinic oils. In certain aspects, the balms and emulsions can include three or more paraffinic oils. In certain aspects, the balms and emulsions can include two or more napthenic oils. In certain aspects, the balms and emulsions can include three or more napthenic oils. The paraffinic and naphthenic oils disclosed herein preferable include a viscosity ranging from 0.5 to 2000 cP, 50 to 1500 cP, 200 to 1250 cP, 500 to 1000 cP, or 750 to 900 cP when included within the emulsions and balms.

As stated above, the disclosed lipophilic carriers solubilize the lipophilic antioxidants provided within the balms and emulsions. In certain aspects, the lipophilic antioxidants include at least one phenolic compound, and in a most preferred aspect, these lipophilic antioxidant may include at least one sterically hindered phenol (hereafter "hindered phenols"). Hindered phenols are primary antioxidants that act as hydrogen donors to effectively neutralize ROS (e.g., free radicals) thereby preventing or reducing the possibility of ROS inducing a deleterious cellular process. In certain aspects, it is advantageous to include the hindered phenols within the balms and emulsion due the chemical nature of these compounds. Specifically, hindered phenols are lipophilic, hydrophobic compounds that can be absorbed by biological membranes having high lipid content (e.g., membranes in the epidermis and dermis). By providing easy absorption through these biological membranes, these antioxidants can also be efficiently absorbed into the blood stream while maintaining a high amount of chemical activity. Thus, the hindered phenols are advantageously included in the disclosed balms and emulsions to potentially reduce intracellular ROS and to potentially treat various maladies including unwanted skin conditions, such as rosacea, psoriasis, acne, eczema, diaper rash, keloid scarring, and combinations thereof.

In certain aspects, the lipophilic antioxidants are included from 0.25 to 50 wt %, 1 to 45 wt %, 1 to 30 wt %, 1 to 10 wt %, 1 to 5 wt %, 1 to 3 wt %, 5 to 40 wt %, 5 to 30 wt %, or 10 to 20 wt % of the overall composition. More preferably, the lipophilic antioxidants are included from 1 to 10 wt % of the overall composition. Most preferably, the lipophilic antioxidants are included from 2 to 4 wt % of the overall composition. The lipophilic antioxidant weight percentages above are preferred because addition of more antioxidant, particularly falling outside the preferred and most preferred ranges, will not improve product efficacy, but will instead only increase manufacturing cost. When the lipophilic carrier (in combination with the lipophilic antioxidant(s)) is provided in a weight percentage falling outside of those above disclosed ranges, precipitation and or loss of efficacy disadvantageously occurs.

The lipophilic antioxidant includes one of the following formulas (I) to (III):

FORMULA I

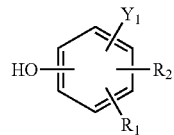

FORMULA II

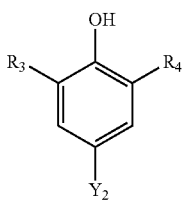

FORMULA III

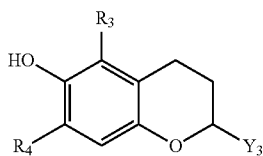

wherein, $R_1$ represents a $C_1$ to $C_9$ linear or branched alkyl group, styrene, or H; $R_2$ is optional and represents a $C_1$ to $C_6$ linear or branched alkyl group, styrene, or H; $Y_1$ represents a $C_1$ to $C_6$ linear or branched alkyl group, styrene, —$SR_5$, or —$(CH_2)_nCOOR_6$; $R_3$ and $R_4$ independently represent a $C_1$ to $C_6$ branched alkyl or H; $Y_2$ represents a $C_1$ to $C_6$ linear or branched alkyl group, —$SR_5$, —$(CH_2)_nCOOR_6$, or H; $Y_3$ represents a linear or branched alkyl group or H; wherein, $R_1$ represents a $C_1$ to $C_9$ linear or branched alkyl group, styrene, or H; $R_2$ is optional and represents a $C_1$ to $C_6$ linear or branched alkyl group, styrene, or H; $Y_1$ represents a $C_1$ to $C_6$ linear or branched alkyl group, styrene, —$SR_5$, or —$(CH_2)_nCOOR_6$; $R_3$ and $R_4$ independently represent a $C_1$ to $C_6$ branched alkyl or H; $Y_2$ represents a $C_1$ to $C_6$ linear or branched alkyl group, —$SR_5$, —$(CH_2)_nCOOR_6$, or H; and $Y_3$ represents a linear or branched alkyl group or H.

In certain aspects, n is from 1 to 10, 1 to 5, 1 to 3, 2 to 6, or 3 to 7. In certain aspects, it is preferable that the compounds are pharmaceutically acceptable compounds or salts thereof.

With regard to Formula I, OH, $Y_1$, $R_1$, and $R_2$ can be in the ortho, meta, and para positions relative to each other.

In certain aspects, the $C_1$ to $C_9$ linear or branched alkyl group of $R_1$, and the $C_1$ to $C_6$ linear or branched groups of $R_2$, $R_3$, $R_4$, $Y_1$, $Y_2$, and $Y_3$ can independently represent, for example, a methyl group, an ethyl group, a propyl, a butyl, a pentyl group, a hexyl group, an isopropyl group, an isobutyl group, a sec-butyl group, a tert-butyl group, a tert-pentyl group, a neo-pentyl group, an isopentyl group, an isohexyl group, or a neohexyl group. In certain aspects, the $C_1$ to $C_9$ group of $R_1$ is a nonyl group. In certain aspects, the $C_1$ to $C_6$ linear or branched alkyl groups of $Y_1$ and $Y_2$ may be substituted with:

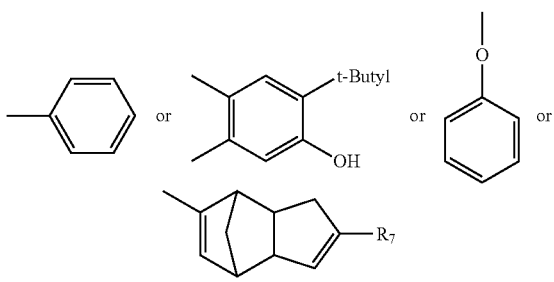

and wherein $R_7$ represents

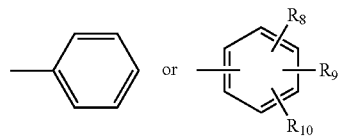

and wherein $R_8$, $R_9$, and $R_{10}$ independently represent OH, a methyl group, ethyl group, a propyl group, a butyl group, an isopropyl group, a tert-butyl group, an isoprene, or a tert-pentyl group, and wherein at least one of $R_8$, $R_9$, and $R_{10}$ is OH. $R_8$, $R_9$, and $R_{10}$ can be in any of the ortho, meta, and para positions relative to each other.

In certain aspects and as defined herein, styrene of $R_1$, $R_2$, and $Y_1$ can include substituted benzene and independently represents

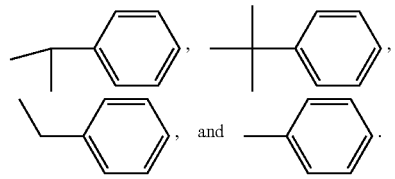

In certain aspects, $R_5$ represents a $C_1$ to $C_{30}$ linear or branched alkyl group or a substituted or unsubstituted aryl group. In certain aspects, $R_5$ represents isoprene, a methyl group, an ethyl group, a propyl, a butyl, a pentyl group, a hexyl group, an isopropyl group, an isobutyl group, a sec-butyl group, a tert-butyl group, a tert-pentyl group, a neo-pentyl group, an isopentyl group, an isohexyl group, or a neohexyl group. In certain aspects, $R_5$ represents,

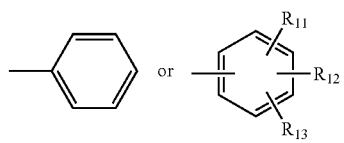

wherein $R_{11}$, $R_{12}$, and $R_{13}$ independently represent OH, a methyl group, ethyl group, a propyl group, a butyl group, an isopropyl group, a tert-butyl group, an isoprene, or a tert-pentyl group, wherein at least one of $R_{11}$, $R_{12}$, and $R_{13}$ is OH. $R_{11}$, $R_{12}$, and $R_{13}$ can be in any of the ortho, meta, and para positions relative to each other.

In certain aspects, $Y_3$ represents an alkyl group having $C_{10}$ to $C_{30}$. In certain aspects, this $C_{10}$ to $C_{30}$ alkyl group may be saturated or unsaturated and may be linear or branched. In certain aspects, it is preferred that this $C_{10}$ to $C_{30}$ alkyl group is saturated having $C_nH_{2n+1}$. In certain aspects, it is preferred that $Y_3$ represents an alkyl group having $C_{12}$ to $C_{20}$ and is preferably $C_nH_{2n+1}$. In most preferred aspects, $Y_3$ represents $C_{15}H_{31}$, $C_{16}H_{33}$, $C_{17}H_{35}$, $C_{18}H_{37}$, $C_{19}H_{39}$, or $C_{20}H_{41}$.

In certain aspects, the compound disclosed in Formula III can be stereo specific or non-stereo specific. Specifically, the carbon linked to $Y_3$ is an asymmetric center. The compound disclosed in Formula III can include a racemic mixture of R, S compounds, only R compounds, or only S compounds. In certain aspects, it is preferable that the compounds of Formula III are a racemic mixture of R, S compounds. In certain aspects, it is preferable that the compounds of Formula III are only R compounds. In certain aspects, it is preferable that the compounds of Formula III are only S compounds.

Specific examples of the antioxidants from Formula I include, but are not limited to, the following:

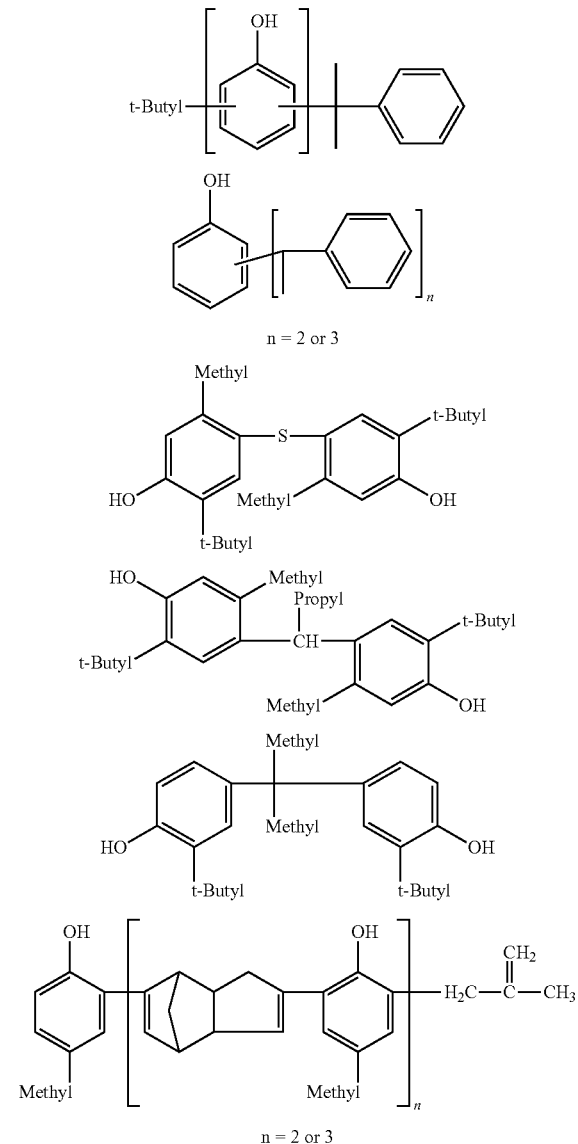

Specific examples of the antioxidants from Formula II include, but are not limited to, the following:

In certain aspects, the lipophilic antioxidants specifically include at least one of an isobutylenated methylstyrenated phenol, a styrenated phenol, various o-, m-, p-cresols (e.g., 4,4'thiobis-6-(t-butyl-m-cresol), 4,4'-butylidenebis-b-(t-butyl-m-cresol)), 2,6-di-tert-butyl-p-cresol, (octadecanoxy-carbonylether) phenol, tetrakis-(methylene-(3,5-ditertbuty-4-hydrocinnamate)methane, 2,2'-methylenebis (4-methyl-6-nonyl)phenol, 1,3,5-tris(3,5-di-tert-butyl-4-hydroxybenxyl-)-1,3,5-triazine-2,4,6 (1H, 3H, 5H)-trione, and combinations thereof within the emulsions and balms.

In certain aspects, the lipophilic antioxidants specifically include at least two, three, four or five of an isobutylenated methylstyrenated phenol, a styrenated phenol, various o-, m-, p-cresols (e.g., 4,4'thiobis-6-(t-butyl-m-cresol), 4,4'-butylidenebis-b-(t-butyl-m-cresol)), 2,6-di-tert-butyl-p-cresol, (octadecanoxycarbonylether)phenol, tetrakis-(methylene-(3,5-ditertbuty-4-hydrocinnamate)methane, 2,2'-methylenebis(4-methyl-6-nonyl)phenol, 1,3,5-tris (3,5-di-tert-butyl-4-hydroxybenxyl-)-1,3,5-triazine-2,4,6 (1H, 3H, 5H)-trione, and combinations thereof within the emulsions and balms.

Additional skin penetration enhancers including, but not limited to, organic solvents and/or surfactants that aid in penetration of the epidermis and dermis may also be included within the disclosed emulsions and balms. Examples of organic solvents included within the disclosed formulations may include, but are not limited to, dimethyl sulfoxide, azone (1-dodecylazacycloheptan-2-one or laurocapran) and pyrrolidones (e.g., N-methyl-2-pyrrolidone.) Examples of surfactants included within the disclosed formulations may include, but are not limited to, linear alkylbenzenesulfonates, lignin sulfonates, fatty alcohol ethoxylates, alkylphenol ethoxylates, various lactate ethers, ethylene glycol, glycerol, propylene glycol, diethylene glycol, dimethyl isosorbide, various fatty acids, including but not limited to, stearic acid, stearates, stearic acid derivatives, palmitic acid, palmitates, palmitic acid derivatives, arachidic acid, arachidic acid derivatives, arachidonic acid, arachidonic acid derivatives, oleic acid, oleic acid derivatives, linolenic acid, linolenic acid derivatives, or any combination thereof. For example, preferred stearic acid derivatives include, but are not limited to, an of Steareth-3, Steareth-5, Steareth-8, Steareth-14, Steareth-16, Steareth-21, Steareth- 25, Steareth-27, Steareth-30, Steareth-40, Steareth-50, Steareth-80, Steareth-100, Steareth-200, which are polyethylene glycol ethers of stearic acid. In certain aspects, the surfactants may include any combination of Steareth-3, Steareth-5, Steareth-8, Steareth-14, Steareth-16, and Steareth-21. Additional skin penetration enhancers included within the disclosed formulations may include urea, oxazolidinones (e.g., 4-decyloxazolidin-2-one), terpenes, and terpenoids. At least one or any combination of the above mentioned skin penetration enhancers can be included at an overall combined concentration ranging from 1 to 10 wt %, more preferably from 2 to 8 wt %, and most preferably from 3 to 5 wt % of the overall composition. In certain aspects, additives including any combination of aloe vera, aloe vera extract, D-Ascorbic Acid, L-Ascorbic Acid, D and L-Ascorbic Acid, glycerin, lilac, and silicone based additives may be included in the emulsion or balm at concentrations ranging from 10 to 40 wt %, 18 to 35 wt %, 25 to 35 wt %, or 28 to 32 wt % of the overall composition.

In certain aspects, various preservatives (e.g., stabilizers) and fragrances can be added to increase shelf life of the disclosed formulations, as well as enhancing the aesthetic aroma/smell of these formulations. In certain aspects, these preservatives, fragrances, or the combination thereof can be present within the disclosed emulsions and balms at a concentration of 0.5 to 5 wt %, 0.75 to 3 wt %, 1 to 2 wt % with the preferred concentration being approximately 1%. Fragrance types can include botanical derivatives, or manufactured chemical fragrances, like those used in soap making. Preservatives (e.g., stabilizers) may include, but are not limited to, formulations having any combination of the following: propylene glycol, propylparaben, methylparaben, diazolidnyl urea, neem oil, sweet orange oil, potassium sorbate, benzylalcohol, tetrasodium EDTA, phenoxyethanol, iodopropynyl, and hydantoin. For example, in certain aspects, the preservative, Germaben II, may be included within the disclosed formulations.

Methods of Making Emulsions and Balms

In certain aspects, the disclosed balms may include the lipophilic carrier and at least one of the lipophilic antioxidants having formulas (I) to (III) disclosed above. When making the disclosed balm, an appropriate amount of the lipophilic carrier and the appropriate amount of the at least one lipophilic antioxidant is weighed out and subsequently mixed together. In certain aspects, the lipophilic carrier is admixed with at least one lipophilic antioxidant having formulas (I) to (III) and heated at temperatures ranging from 230-275° F., more preferably from 240-270° F., most preferably from 250-265° F. during a time period from 5-60 min, preferably from 5-15 min, most preferably 5 min. In this mixture referred, to as a master batch, the antioxidant to carrier ratio is very high, for example, approximately a 1:1 ratio by weight in order to solubilize the antioxidant. This mixture will not remain liquid and flow able at room temperature. And only serves to disperse the melted antioxidant into the batch without the need to heat the entire mass. While heating the admixed lipophilic carrier with the lipophilic antioxidant, the admixture will gradually change from a cloudy, precipitous-like appearance to a clear, transparent-like appearance. During this process it is important that the admixture is completely melted so that no solid particles remain. This ensures that the lipophilic antioxidant achieves maximum solubilization within the lipophilic carrier. This is important for two reasons, if the antioxidant particles are too large absorption into the skin is not possible, rendering the product ineffective, and the grainy nature of the antioxidant is unpleasant when applied to the skin.

In certain aspects, the admixture having the lipophilic antioxidant solubilized in the lipophilic carrier may be subsequently added to (e.g., diluted with) an additional lipophilic carrier. This additional lipophilic carrier has also preferably been liquefied before adding the admixture having the lipophilic antioxidant solubilized in the lipophilic carrier. For example, in certain aspects, this additional lipophilic carrier may be a liquefied lipophilic carrier (or a heated oil) contained within an industrial, pharmaceutical-type melt tank. In preferred embodiments, the melt tank has been warmed long enough and to a temperature sufficient to liquefy and/or heat the lipophilic carrier, but not warm enough to boil or flash off the lipophilic carrier. In certain aspects, the industrial, pharmaceutical-type melt tank may be pre-warmed. In certain aspects, the industrial, pharmaceutical-type melt tank has been warmed to a temperature of 100-150° F. preferably 110-130° F., most preferably 120° F. It preferable not to exceed 150° F. to prevent separation of the hydrogenated oil (e.g., avocado butter) from the other ingredients. If heated too long or too hot the butter takes on an unpleasant consistency. In certain aspects, this additional lipophilic carrier may be the same or a different lipophilic carrier than what has been used in the admixture, and in certain aspects, the additional lipophilic carrier may further include additional solvents, surfactants, oils, lipophilic antioxidants having formulas (I) to (III) as disclosed above, or any combination thereof.

As discussed above, the admixture having the lipophilic antioxidant solubilized in the lipophilic carrier is subsequently added to (e.g., diluted) in the additional lipophilic carrier and mixed for 5-60 minutes, more preferably 10-30 minutes, and most preferably 20 minutes while concurrently being heated to ensure overall homogeneity. During this mixing step, fragrance can optionally be added to provide the resulting balm with the desired fragrance. In certain aspects, the resulting mixture can be discharged from the industrial, pharmaceutical-type melt tank into appropriate receptacles (e.g., plastic jars) and allowed to cool and subsequently harden, thus resulting in the disclosed balms.

The emulsion is made by substantially the same process as disclosed above. However, the emulsion further includes a surfactant allowing the oil phase along with the antioxidant and water phase to be properly mixed. In certain aspects, all of the water based ingredients are mixed together and heated to approximately 150° F. Similarly, the oil based ingredients and the surfactants are heated and mixed together. Then once both parts, known as phases, are heated and mixed then they are combined with each other while mixing to form the emulsion. Generally the mixing occurs for the duration of the cool down and the mixer generally is capable of generating high shear forces.

In certain aspects, the disclosed balm may be made without heat and by merely using mechanical means to mix the ingredients (e.g., carrier oil, antioxidant, etc.) to reduce particle size such that the balm may effectively penetrate skin. For example, the following two methods may be used. The first method involves tumbling the ingredients in a sealed container. For example, a liquid tight rotary tumbler may be used, and the tumbling media used is stainless steel ball bearings. In this aspect, the antioxidant powder is weighed out as well as the carrier oil. In certain aspects, Vitamin E oil may also be used. With this method, the ingredients (e.g., lipophilic carrier and antioxidant) are placed into the tumbler at an acceptable ratio of 1:1 to 20:1, more preferably 1:1 to 5:1 and most preferably 1:1. The tumbler, when loaded with media and all ingredients, should be approximately 75% full. The tumbler is turned on and the barrel turns for approximately 12 hours. In certain aspects, the agitation rate ranges from 30 to 80 rpm, 40 to 70 rpm, and 50 rpm to 65 rpm, and 55 rpm to 65 rpm. During this time, the ball bearings pulverize the powder and reduce the particle size significantly. The final product has been tested and will pass through a 325 mesh screen and have a particle diameter ranging from 30 nm to 30) lm, 30 nm to 15) lm, 40 nm to 10) lm, 40 nm to 5) lm, 40 nm to 1) lm, 40 nm to 900 nm, 40 nm to 750 nm, 40 nm to 500 nm, 50 nm to 400 nm, 40 nm to 300 nm, 50 nm to 250 nm, 40 nm to 100 nm, and 40 nm to 70 nm. The ball bearings are separated from the mixture with a sieve and cleaned for reuse.

The second mechanical method involves the use of a high shear mixer, which includes, for example, a Vertishear Tempest machine. The ingredients, which include a powder form of the antioxidant and the carrier oil, are added to an appropriately sized container at a ratio of 1:1 by weight. Similar to the previously described mechanical method, Vitamin E oil may also be used. The mixture is processed in the mixer for approximately 2 hours. It is important to note that the speed of the mixer should be limited. Due to the friction between the solid particles and the high speed mixing blade, heat will be generated. It is important to limit this heat to below 200° F. Otherwise the antioxidant particles will start to melt and fuse together creating a hardened mass that will not mix. In order to avoid this, the speed of the mixer should be controlled, or the mixing performed in cycles allowing the mixture to cool intermittently.

WORKING EXAMPLES

The following discloses an exemplary balm made according to the methods and compositions disclosed herein.

Example 1

Exemplary Balm
1.1 Materials Used
1.1.1 Avocado Butter glorybeefoods.com
1.1.2 IRGANOX® 1010 BASF, having the chemical name Pentaerythritol tetrakis(3-(3,5-di-tert-butyl-4-hydroxyphenyl)propionate) having a molecular weight of 1178 g/mol as specified in BASF's plastic additive's "Technical Information" sheet from September 2010, CAS No. 6683-19-8.
1.1.3 Vitamin E Oil lotioncrafter.com
1.1.4 Fragrance currently using cucumber melon fragrance sourced from soaperafter.com
1.1.5 Scale
1.1.6 Double Boiler
1.1.7 Plastic tamper seal plastic shrink bands provided by sks-bottle.com

| Ingredient | Full Batch Qty. | % |
|---|---|---|
| Avocado Butter | 15 lbs. (240 oz.) | 94 |
| Irganox ® 1010 | 7.65 oz. | 3 |
| Vitamin E Oil | 7.65 oz. | 3 |
| Fragrance | 2 TBSP | |

1.2 Weighing of Raw Materials
NOTE all raw material containers must be sealed at all times and are only opened while in use.
NOTE: ALL materials acceptable variation is 0.1 Unit of Measurement.

1.2.1 Avocado Butter
1.2.1.1 Using "OHAUS® CD-II" scale, be sure that scale is displaying the "oz.", (ounces) setting.
1.2.1.2 Zero out the scale by pressing the "tare" button.
1.2.1.3 Weighed out the correct amount of Avocado butter, and placed into the storage container.
1.2.2 Irganox® 1010 Antioxidant and Vitamin E Oil
1.2.2.1 Using "OHAUS® CD-II" scale, be sure that scale is displaying the "oz.", (ounces) setting.
1.2.2.2 Zero out the scale by pressing the "tare" button.
1.2.2.3 Weighed out the correct amount of IRGANOX® 1010 and place into tumbling canister.
1.2.2.4 Weigh out the correct amount of Vitamin E Oil and place into a tumbling canister.
1.2.2.5 Tumble for 12 hours and place into sealed storage container. This will now be referred to as the "Antioxidant Master Batch."
1.3 Heating Material in Double Boiler
1.3.1 Pre-heat double boiler to 150° F.
1.3.2 Add the measured Avocado butter and Antioxidant Master Batch. Mix thoroughly.
1.3.3 Add fragrance and mix.
1.3.4 Pour contents into dispensing container.

Example 2

Exemplary Emulsion/Lotion
1.0 Materials used
1.1 Part 1 Water Based Ingredients

| Component | Units (g) | Percentage (Wt %) |
|---|---|---|
| 1.1.1 Distilled Water | 2020.00 | 51.53% |
| 1.1.2 Glycerin | 400.00 | 10.20% |

1.2 Part 2 Oil Based Ingredients

| Component | Units (g) | Percentage (Wt %) |
|---|---|---|
| 1.2.1 I-Butter (IRGANOX 1010 BASF & Avocado butter) | 280.00 | 7.14% |
| 1.2.2. Stearic acid | 120.00 | 3.06% |
| 1.2.3 Mineral oil (Lilac) | 400.00 | 10.20% |
| 1.2.4 Sonnocone Petrolatum | 400.00 | 10.20% |
| 1.2.5 Vitamin E | 80.00 | 2.04% |
| 1.2.6 Steareth 2 | 91.72 | 2.34% |
| 1.2.7 Steareth 21 | 48.28 | 1.23% |

1.3 Part 3 Cream stabilizer and preservative

| Component | Units (g) | Percentage (Wt %) |
|---|---|---|
| 1.3.1 GERMABEN II | 10.00 | 0.25% |
| 1.3.2 Fragrance | 70.00 | 1.78% |

2.0 Procedure
2.1 All batches were made by weight percentage ratios.
2.2 Heated up the I 1010 and Avocado Butter in correct weight percentage ratios (e.g., a 2.5:1 I 1010:Avacado Butter, or more preferably a 3:1 ratio of Avocado Butter:I 1010) to produce I-Butter.
2.2.1 Kept on low heat and set aside for Part 2 mixture.
2.3 Part 1 Mixture
2.3.1 Using cooking scale measured out all ingredients for Part 1 Water Based Ingredients based off of Percent composition shown in 1.1 above.

2.3.2 Add all ingredients to heated container and mix thoroughly 2.3.2.1 Part 1 Water Based Ingredients are heated and mixed to between 150° F.-200° F. without allowing Part 1 to boil 2.4 Part 2 Mixture 2.4.1 Measured out all ingredients for Part 2 Oil Based Ingredients based off of Percent composition shown in 1.2 above.

2.4.2 Added all ingredients to a separate heated container and mixed thoroughly 2.4.2.1 Made sure to heat all granules to a liquid in the Part 2 mixture, failure to do so will result in grainy lotion cream leading to a defective product 2.4.2.2 Part 2 Oil Based Ingredients were heated and mixed to between 150° F.-200° F. without allowing Part 2 to boil.

2.5 Part 3 Mixture 2.5.1 Using cooking scale measured out all ingredients for Part 3 Cream stabilizer and preservative based off of Percent composition shown in 1.3 above.

2.5.2 Combined the two ingredients and placed to the side 2.6 Combining Mixtures Parts 1, 2, and 3

2.6.1 After Parts 1 and 2 have reached a temperature ranging from between 150° F.-200° F.

2.6.2 Combined Part 1 and 2 mixtures together. Thoroughly blended the two mixtures together in the homogenizer at 2,800 rpm.

2.6.3 New mixture containing Part 1 and 2 must reach a temperature below 150° F., continuously mixed new mixture until temperature was attained 2.6.4 Once the mix has reached 160° F. add Part 3 while continuing to mix.

2.6.5 Place the mix from the previous step into the homogenizer at 2,800 rpm until there was no frothy head of foam on top of lotion and then dispensed into appropriate container, approximately 30 minutes.

2.6.6 Add the mixture from part 3 to the homogenizer and mix for 30 minutes at 2,800 rpm.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A method of making a topical composition comprising:
   mixing a lipophilic antioxidant comprising at least one phenyl group and a lipophilic carrier to create a butter and heating to 230-275° F. for about five minutes;
   mixing water and glycerin in a container and heating to between 150-200° F. to create a water-glycerin mixture;
   mixing the butter with a surfactant, a mineral oil, a paraffinic oil, an antioxidant, a skin penetration enhancer and heating to between 150-200° F. to create an oil-based mixture;
   mixing a preservative with a fragrance to create a preservative mixture;
   mixing the water-glycerin mixture with the oil-based mixture to create an emulsion and reducing temperature; and
   mixing in the preservative mixture once temperature has reached about 160° F. and cooling to room temperature.

2. The method of claim 1 wherein the lipophilic antioxidant is pentaerythritol tetrakis (3-(3,5-di-tert-butyl-4-hydroxyphenyl) propionate).

3. The method of claim 1 wherein the lipophilic carrier is avocado butter.

4. The method of claim 1 wherein the paraffinic oil is petrolatum.

5. The method of claim 1 wherein the antioxidant is vitamin E.

6. The method of claim 1 wherein the skin penetration enhancer comprises at least one derivative of stearic acid.

7. The method of claim 1 wherein the preservative mixture comprises propylene glycol, diazolidinyl urea, methylparaben, and propylparaben.

* * * * *